United States Patent [19]

Schmidt

[11] Patent Number: 5,683,462

[45] Date of Patent: Nov. 4, 1997

[54] ARTIFICIAL BONE REPLACEMENT DEVICES INCLUDING FLEXIBLE JOINT STRUCTURES FOR USE IN CADAVERS

[76] Inventor: Roderic H. Schmidt, 2544 Swan Blvd., Milwaukee, Wis. 53226

[21] Appl. No.: 610,407

[22] Filed: Mar. 4, 1996

[51] Int. Cl.$^6$ .................................. A61F 2/28; A61F 2/50
[52] U.S. Cl. .................................................. 623/16; 623/66
[58] Field of Search ........................... 403/220, 223, 403/291; 623/16

[56] References Cited

U.S. PATENT DOCUMENTS

| | | | |
|---|---|---|---|
| 4,258,441 | 3/1981 | Bell | 3/12.6 |
| 4,852,554 | 8/1989 | Alten | 128/68 |
| 4,863,473 | 9/1989 | Glowczewski, Jr. | 623/16 |
| 5,433,549 | 7/1995 | McGaffigan | 403/229 |

*Primary Examiner*—David Isabella
*Assistant Examiner*—John M. Black
*Attorney, Agent, or Firm*—Andus, Sceales, Starke & Sawall

[57] ABSTRACT

An artificial bone replacement device includes opposite end connectors interconnected to each other by a flexible unit consisting of an outer plastic tube and an inner plastic tube. The flexible telescoped tubes provide a flexible joint permitting angular movement of the connectors relative to each other. The connector are constructed for connection to a bone structure of a cadaver or to a bone replacement element in a cadaver such as a tubular member. A shoulder replacement device includes a first connector having a projecting screw member for threading into the collar bone. The opposite connector includes a tubular member connected to the tubular plastic tubes and having an opposite outer end tubular connector for interconnection to a bone or an artificial replacement member. The tubes are secured to the connectors by a cross screw threaded through the respective connectors and tubes. A similar screw is provided to connect the outer tubular connector to the bone or a bone replacement element. The replacement device can be constructed with the screw members at the opposite end or with both end connectors formed as tubular members for telescopic reception of bone structure or bone replacement elements.

12 Claims, 1 Drawing Sheet

ARTIFICIAL BONE REPLACEMENT DEVICES INCLUDING FLEXIBLE JOINT STRUCTURES FOR USE IN CADAVERS

BACKGROUND OF THE INVENTION

This invention relates to an artificial bone replacement device having a flexible joint and particularly such device for insertion into a cadaver to permit display of the deceased at a wake or the like.

The present inventor has previously developed adjustable elongated members for the replacement of a bone or bones within a cadaver. As more fully disclosed in the inventor's co-pending application entitled "ARTIFICIAL BONE REPLACEMENT FOR CADAVERS", filed on Apr. 14, 1994 with Ser. No. 08/227,684, and the issued as U.S. Pat. No. 5,496,373 on Mar. 5, 1996, bone reconstruction in cadavers and/or bone replacement has been developed as the demand has increased for bones as transplant to living persons made from the body of a deceased donor. Harvesting of the bones essentially immediately after the death of the donor is of substantial significance. There has been substantial development of an elongated replacement member with interconnected adjustable constructions for adjustment of the length to the requirement of a particular body. The above-identified patent application of the inventor provides a particularly cost effective system for replacement of elongated bone structures.

In addition to straight bone structure replacement, the joints of the deceased may often also require attention and restructuring. Thus, an elbow may desirably be restructured. Destruction in the ankle area of the deceased may also require reconsideration. The shoulder structure of the deceased may also require certain reconsideration and with present day technology, a shoulder structure may be wholly or partially removed for purposes of transplant. All of these joints would generally require restructuring or replacement, preferably with a structure having an appropriate joint construction to permit the proper orientation of the deceased limbs with respect to each other and with respect to the main body structure. Generally, the present inventor knows of no highly satisfactory replacement artificial replacement device for joint applications and particularly for elbows and ankles. U.S. Pat. No. 4,852,554, which issued on Aug. 1, 1989, entitled "Reconstructive Orthopedic Devices For Cadavers" as well as the inventor's identified '373 patent disclose a simple fixed pivot construction within an elongated assembly for elbow replacement. In the above '554 patent, two rigid bone replacement members are formed with a special joint having a fixed pivot point. In the illustrated structure, an enlarged tubular member defining one part of the pivotal joint has a slot on one side. A second tubular member is telescoped into the slotted end and is connected therein by a pivot pin defining a fixed pivotal support point. The inserted member has its end face formed with a substantial chamfered or inclined end to permit the pivotal movement within the slotted end. Although such a structure does provide for some pivotal motion, it requires a single directional orientation, with other means provided if relative relationship of the bone is to be offset in a direction other than that provided by the pivot pin. As a result, the structure has application in a limited specific arrangement and does permit optimal positioning in many instances. The system, for example, is not particularly suitable for shoulder, ankle and like reconstruction.

As a result of the increasing demand in the reconstruction of cadavers, there is a demand for a more versatile and cost effective flexible joint and particularly such a replacement device which is cost effective both structurally and in installation.

SUMMARY OF THE PRESENT INVENTION

The present invention is particularly directed to an artificial bone replacement device having an semi-flexible artificial joint in which first and second bone coupling members are interconnected to each other through a semi-flexible and suitable member. Thus, depending upon the particular joint which needs reconstruction, the bone replacement device includes end members specially constructed for interconnection to the structure to the opposite sides of the replaced joint bone structure of the cadaver's joint. An elongated semi-flexible member having a limited flexibility is interconnected between the facing ends of the two end members and is formed of an appropriate length, which can be made adjustable in a preferred construction, to permit the orientation of the end members as required. The flexible members support the two end members in properly spaced relation and allows relative orientation thereof in essentially any direction. A tubular plastic member of a proper wall thickness is one example of a suitable joining member. The present inventor has found that a particularly satisfactory and unique flexible joining member consisting of a pair of telescoped plastic tubing, one of which tends to set in a bent location and a second which tends to reset to the original position.

More particularly, in a shoulder replacement structure, the shoulder replacement device included a first shoulder connector unit having a connecting element or member for interconnection into the exposed collar bone upon removal of the shoulder bone structure. The shoulder connector unit is preferably a threaded screw member. An opposite end arm connector unit includes a coupling or connecting member for connection to the arm bone or to an artificial bone replacement member for such arm bone. The arm connector unit generally includes of a cup-shaped and tubular coupling or connecting member adapted to be telescoped over an artificial bone replacement member or otherwise secured in place. The shoulder connector unit may be formed with a rotating connection within the connection to permit the turning of the threaded member into the shoulder bone.

The bone members are connected by a flexible joint element such as the telescoped plastic tubes. An elbow replacement may include the flexible member interconnected directly between an elongated bone replacement member. Thus, a telescoped upper arm structure and a telescopic lower arm bone replacement device may be connected to each other through the flexible unit such as the telescoped plastic tubes. The telescopic arm members coupled together may be constructed in accordance with any of the teachings of the prior art, and preferably, using the teaching of the inventor's prior patent application.

The present invention provides a highly cost effective and improved joint structure for replacement of flexible joints of a cadaver. The components are readily formed, in the preferred constructions, from available plastic tubing and are readily available or may be mass produced as plastic molded parts and the like. The assembly is simple and straight forward using any suitable interconnecting elements or devices which maintain the appropriate interrelationship between the component parts while permitting ready and reliable attachment to the remaining bone structure of the cadaver.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DESCRIPTION OF THE ILLUSTRATED EMBODIMENTS

Figure 1:
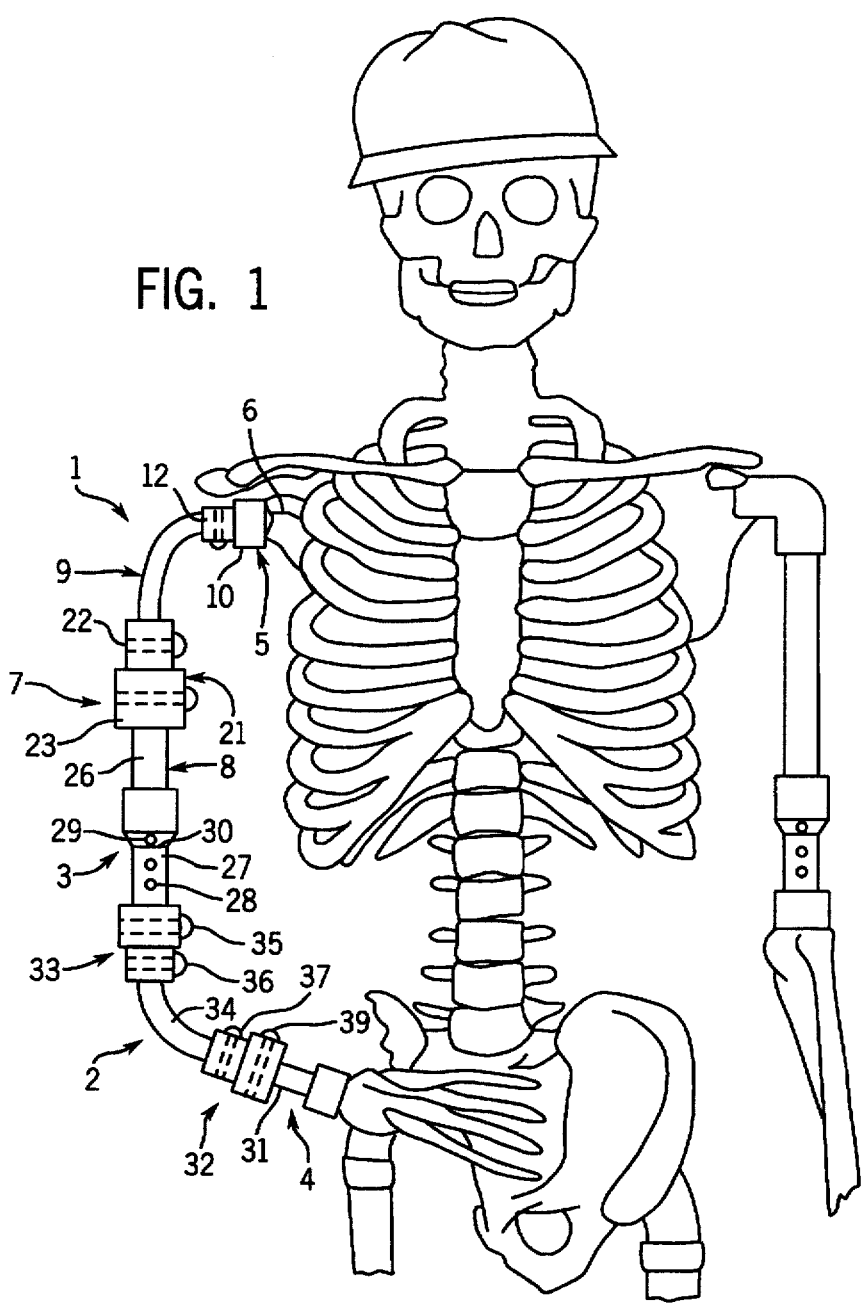
FIG. 1 is a fragmentary illustration of a bone structure of a cadaver body particularly illustrating a reconstructed shoulder unit and a reconstructed elbow unit, in accordance with one embodiment of the present invention.

Referring to the drawings and particularly to FIG. 1, the bone structure of a cadaver is illustrated incorporating a reconstructed shoulder device 1 and a reconstructed elbow device 2, both of which include a flexible connecting member and illustrate the embodiments of the present invention.

The arm structure 3 connected to the shoulder device 1 and to the elbow device 2 is illustrated in accordance with the structure illustrated in the inventor's '373 patent. The second or forearm structure 4 interconnected to the opposite side of the elbow device 2 is illustrated connected to a portion of the forearm for simplicity and clarity of description. The opposite arm is shown with a construction as shown in the '373 patent. The other parts of the body, illustrated, would of course be the conventional cadaver construction.

Figure 2:
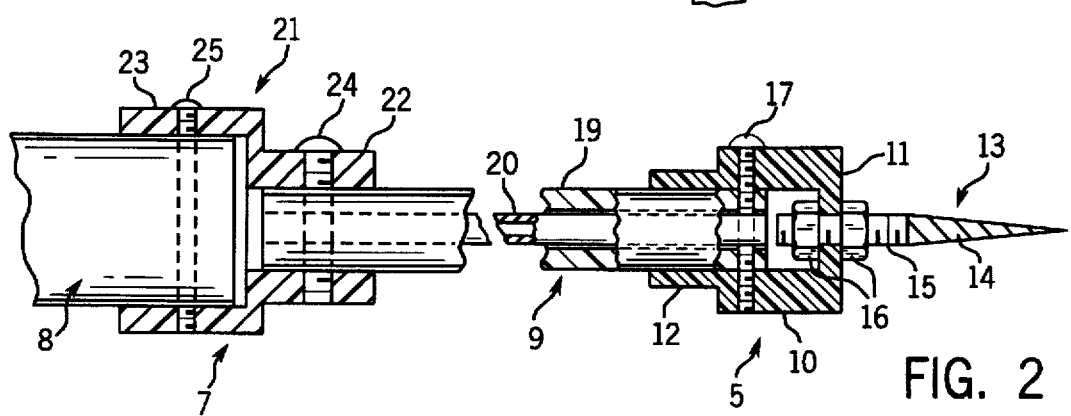
FIG. 2 is an enlarged axial cross-section through the reconstructed shoulder unit illustrated in FIG. 1.

Referring more particularly to FIGS. 1–2, a practical and preferred construction of the artificial bone replacement shoulder device 1 is more clearly illustrated and described as follows.

Generally, in the illustrated embodiment of the invention, the shoulder device 1 includes a collar bone connector unit 5 for fixed interconnection to the remaining collar bone 6 of the cadaver. The shoulder device 1 further includes an opposite arm connector unit 7 adapted to be fixedly connected to the upper end of the arm structure 3 for the cadaver, which is shown as a bone replacement member 8 such as shown in the prior art. The connector unit 5 and the arm connector unit 7 are interconnected to each other by a elongated flexible unit 9.

The flexible unit 9 preferably has a limited flexibility, such that with the opposite end members interconnected, for example, to the shoulder bone or collar 6 and the member 8 of the cadaver, the flexible unit 9 can be bent and oriented to locate and support the arm structure 3 relative to the shoulder connection in a realistic desired orientation. The flexible unit 9 is thus bendable and provides a firm adjustable interconnection while eliminating a rigid interconnection having a simple single motion between the shoulder and arm, as generally provided in the prior art.

More particularly in the illustrated embodiment of the invention as clearly shown in FIGS. 1 and 2, the collar bone connector unit 5 includes a generally cup-shaped and stepped end cap 10 having an outer base 11 and a tubular stepped rim 12. A bone anchor or attachment screw 13 is secured to the base 11 with an outer screw portion 14 and an inner threaded portion 15 projected through the base. The screw 13 a self tapping securement screw and is anchored to the base by clamping nuts 16 threaded on the exterior and interior threaded portion in accordance with the '373 patent.

The stepped cap is a tubular coupling or connecting member. The flexible unit 9 is shown as a tubular unit having an outer diameter corresponding to the diameter of the cap 10. The unit 9 is inserted into the cap 10 and secured in place in any suitable manner. In the illustrated embodiment, a screw 17 is threaded through the cap 10 and the inserted end of the flexible unit 9 to firmly secure them to each other.

As previously described, the arm connector device 7 is similarly connected to the unit 9 and fixed to arm member 8.

The tubular unit 9 is illustrated in a preferred construction including an outer tubular member 19 and an inner tubular member 20. The outer tubular member 19 is a relative resilient plastic member while the inner tubular member 20 is a substantially less resilient member and tends to take shape. The tubular unit 9 thus permits bending to provide the interconnected orientation of the shoulder connector unit 5 and the arm connector unit 7 into place with the arm and hand located in substantial relation to the removed bone structure and providing a realistic placement of the upper shoulder and arm member 8 within the body tissue enclosures (not shown) therefor.

Thus, the arm connector device 7 includes a stepped tubular member 21 having a connecting portion 22 connected to unit 9 and an arm connecting portion 23 connected to arm member 8. The tubular unit 9 is inserted in connecting portion 22 and is shown secured in place by a self-tapping screw 24 extending laterally through the portion 22 and unit 9 in the manner of the attachment screw 17.

The arm member 8 is telescoped into the outer enlarged tubular portion 23 and is similarly secured in place by an interconnecting self-tapping screw 25.

The arm member 8 is shown including telescoping tubes 26 and 27, one which include a plurality of openings 28 and the other including a single opening 29 to allow length adjustment. A connecting wire 30 is passed through aligned openings 28–29 and laid along the tubes to provide a compact connection, such as shown in the '373 patent.

The end connection means should provide a reliable and stable interconnection to the other body portions of the cadaver and allow the subsequent reliable manipulation and movement of the body for embalming and display while maintaining a most realistic presentation.

The opposite or other end of member 8, formed by tube 27, is connected by the elbow device 2 to the forearm bone 4.

The forearm may consist of the cadaver bone as illustrated or may be a replacement arm member such as shown in the '373 patent or other suitable device. If the bone remains, the unit 7 may include an attachment screw assembly such as connection unit 5 of the shoulder device 1, or a tubular unit 31 for direct connection to the bone 4. If the forearm 4 also includes an adjustable bone replacement, the elbow device 2 is formed with similar tubular end connector unit for connection to the upper arm replacement member 8 and the forearm replacement member 31.

More particularly, as shown in FIG. 1, the elbow device 2 includes tubular stepped connector members or units 32 and 33 connected to each other by a flexible tubular unit 34. Each of the tubular stepped connector units 32 and 33 are constructed as shown for stepped tubular member 21 of the shoulder device. Unit 33 is connected to member 27 of arm structure 3 and secured to unit 33 by a 35 and bone 4 connected to unit 32 by 36 Unit 33 is secured to the tubular unit 34, which corresponds in structure to that of unit 9, by an attachment screw 36. Unit 32 is connected to the tube 34 by an attachment screw 37 and to bones 4 by a screw 39. The elbow device 2 again permits the orientation of the forearm structure relative to the upper arm structure for realistic arrangement of the cadaver.

The stepped members are conveniently formed from tubular members of related inner/outer diameters. For example, the end connectors with attachment screws are conveniently formed from a large diameter end cap member in combination with a smaller tubular member having an outer diameter corresponding to the inner diameter of the cap member. The plastic members are readily telescoped and firmly interconnected to each other through the use of a suitable adhesive, in the same manner as heretofore used in various practical implementations of bone replacement devices. Although the end screw connectors and the interconnection of the telescopic elongated members are preferably constructed in accordance with the subject '373 patent and such construction is not critical to the satisfactory implementation of the highly flexible and generally universal adjustable elbow or flexible joint structure as suggested by the present invention.

Thus, the flexible element provides for adjustment in a plurality and effectively infinite different number of planes with the illustrated embodiment. Thus, it permits both the vertical and lateral, as well as angular orientation, of the arm structure and the interconnection thereof to the body structure. The system maintains a relatively compact replacement bone structure which can be readily enclosed within the body tissue in accordance with normal practice of enclosing the bone replacement structures of the prior art, while maintaining the significant increase versatility in appropriate orientation of the bone replacement devices and the interconnected remaining bone body parts.

The various embodiments of the present invention have been disclosed in a preferred construction. However, those skilled in the art will readily recognize that the flexible element and the end connectors may take many different forms for producing a highly presettable member movable in a plurality of planes with various interconnections to the cadaver and the flexible element. Thus, the flexible element can be any structure providing a reliable multiple positioning arrangement with respect to the end connectors so as to permit the appropriate orientation of the replacement bone elements with a flexible interconnection which can more effectively be located in relationship to the original bone structure. Thus, within the broadest aspect of the present invention, a multiple linkage structure permitting pre-angular orientation and curvatures, may be used within the broadest aspect of the present invention as a part of a bone replacement mechanism. The flexible plastic unit, particularly with the dual tubular telescoped or arranged members, has been found to provide a particularly practical and effective supporting arrangement at a particularly cost effective device. The end connection can be made from readily available tubular components, such as used heretofore in other bone replacement structures, and the system is particularly adapted to continued use of the highly effective adjustable and screw mounting of the inventor's '373 patent.

Various modes of carrying out the invention are contemplated as being within the scope of the following claims particularly pointing out and distinctly claiming the subject matter which is regarded as the invention.

I claim:

1. An artificial bone replacement device for replacement of a removed bone joint structure of a cadaver, said joint structure having a first existing bone member and a second existing bone member, comprising a first connector unit for connection to the first existing bone member of the removed joint structure of the cadaver, a second connector unit for connection to the second existing bone member of said cadaver for the same removed joint structure, an elongated flexible unit connected to said first and second connection units, said elongated flexible unit being bendable about an intermediate location between said connector units into a plurality of different planes for essentially unrestricted preset orientation of said connected first and second existing bone members in a single plane and in any one of said plurality of different planes relative to each other and holding said existing bone members in said preset orientation.

2. The bone replacement device of claim 1 wherein said elongated flexible unit includes a plastic unit permitting manual setting of said connector units in said preset orientation.

3. The bone replacement device of claim 2 wherein said plastic unit includes a first plastic member and a second plastic member, said first plastic member having a substantial greater resiliency than said second plastic member, and both said first and second plastic members being secured to said first and second connector units.

4. The bone replacement device of claim 2 wherein said plastic unit includes a first plastic tube and a second plastic tube within said first plastic tube, said plastic tubes being readily bent to angularly offset said connector units with one of said plastic tubes being substantially stiffer than the other one of said outer plastic tubes.

5. The bone replacement device of claim 1 wherein said flexible unit is a flexible plastic unit, wherein at least one of said connector units includes an attachment screw for embedding into the existing natural bone structure of a cadaver.

6. The bone replacement device of claim 1 wherein said flexible unit is a flexible plastic unit, wherein at least one of said connector units includes a tubular coupling member for said connection to said bone member, and a connecting member passing through the coupling member and a bone member for securing the connector unit in place.

7. A shoulder replacement device for replacing the shoulder structure of a cadaver, said shoulder structure having a collar bone and an arm member, comprising a first connector unit having an attachment element for embeddment in the collar bone of a cadaver, a second connector unit for connection to the arm member of the cadaver, and an elongated semi-flexible unit connected between said first and second connector unit, said semi-flexible unit being bendable in a plurality of planes for angularly offsetting said connector units in the same plane or into different planes relative to each other and thereby orient said arm member relative to said collar bone.

8. The shoulder replacement device of claim 7 wherein first connector unit includes a base having an opening, said attachment element includes a self-tapping screw having a threaded portion extended through said opening in said base, and first and second clamping member secured onto said threaded portion to the opposite side of said opening and abutting said base to firmly secure the screw to the base.

9. The shoulder replacement device of claim 7 wherein said second connector unit includes a tubular connector member for receiving said arm member, and a connecting member for extending through the connector unit and the arm member.

10. The shoulder replacement device of claim 9 wherein said connecting member is a self-tapping screw threaded through said tubular connector member and said arm member.

11. An elbow replacement device for replacing an elbow structure of a cadaver, comprising a first connector unit for attachment to an upper arm bone of a cadaver, a second connector unit for attachment to a lower bone of a cadaver, an elongated semi-flexible unit connected between said first and second connector unit, said semi-flexible unit being bendable in a plurality of planes for angularly offsetting said connector units in the same plane or in different planes relative to each other and orient said upper and lower bones relative to each other.

12. The elbow replacement device of claim 11 wherein said first and second connector units include a tubular end portion for receiving said upper and lower bones, and self-tapping screws passing through said tubular end portions and said upper and lower bones for firmly securing the connector units to the upper and lower bones.

* * * * *